United States Patent [19]

Kuraoka

[11] 4,428,684
[45] Jan. 31, 1984

[54] APPARATUS FOR MEASURING MELTING POINT AND BOILING POINT OF GAS

[75] Inventor: Yasuo Kuraoka, Sapporo, Japan

[73] Assignee: Hoxan Corporation, Sapporo, Japan

[21] Appl. No.: 337,078

[22] Filed: Jan. 4, 1982

[30] Foreign Application Priority Data

Jan. 30, 1981 [JP] Japan ................................. 56-12607

[51] Int. Cl.³ ...................... G01N 25/04; G01N 25/08
[52] U.S. Cl. .................................................... 374/25
[58] Field of Search ....................... 374/16, 17, 25, 27, 374/28

[56] References Cited

U.S. PATENT DOCUMENTS

| | | | |
|---|---|---|---|
| 2,672,751 | 3/1954 | Lupfer et al. | 374/25 |
| 3,143,876 | 8/1964 | Wallgren | 374/17 |
| 3,250,115 | 5/1966 | Donnell | 374/25 |
| 3,695,093 | 10/1972 | Hummell et al. | 374/25 |
| 3,994,164 | 11/1976 | Regenass et al. | 374/31 |

*Primary Examiner*—Herbert Goldstein
*Attorney, Agent, or Firm*—George B. Oujevolk

[57] ABSTRACT

A sample cell is located in an inner tank which is surrounded by a heat insulating container. Inert gas is circulated through the inner tank from separate heating and cooling paths. A pressure regulator is located in the sample cell.

1 Claim, 2 Drawing Figures

APPARATUS FOR MEASURING MELTING POINT AND BOILING POINT OF GAS

BACKGROUND OF THE INVENTION

This invention relates to an apparatus for measuring the melting point and boiling point of a gas to obtain the purity and the mixture ratio of sample gases.

A variety of methods for measuring, for example, with a gas chromatograph or the like the purity of a sample gas such as benzene or the mixture ratio of several gases in mixed gases have heretofore been measured but the measuring operation is complicated and the apparatus for measuring gases is very expensive.

Accordingly, it has already been considered to obtain the purity and the mixture ratio of sample gases by measuring the melting point and the boiling point of the sample gases by utilizing the fact that the melting point and the boiling point of a gas will vary according to the amount of impurities contained in the sample gas and because the melting point and the boiling point of a gas exhibits a predetermined value in accordance with the mixture ratio of the mixed gases, but the conventional measuring method cannot obtain highly accurate measured results of the melting point and the boiling point of a gas. Accordingly, the measurement of the purity or the like is done by using a gas chromatograph or the like.

OBJECTS OF THE INVENTION

Accordingly, a primary object of this invention is to provide an apparatus for measuring the melting point and the boiling point of a gas, which can precisely measure the melting point and the boiling point of the gas.

Another object of this invention is to provide an apparatus for measuring the melting point and the boiling point of a gas which can be operated simply and inexpensively.

Yet another object of this invention is to provide an apparatus for measuring the melting point and the boiling point of a gas which can precisely control the sample gas at a temperature so as not to be effected thermally by the external temperature.

A further object of this invention is to provide an apparatus for measuring the melting point and the boiling point of a gas which can raise or lower the temperature of the sample gas as desired with fine adjustments in the temperature changes.

Still another object of this invention is to provide an apparatus for measuring the melting point and the boiling point of a gas which can raise or lower the temperature of the sample gas in accordance with the phase state of the sample gas and upon request can measure the melting point or the boiling point of the gas with rapid and simple operations.

Still another object of the invention is to provide an apparatus for measuring the melting point and the boiling point of a gas which can improve the reliability of the results by further measuring the melting point and the boiling point of the same sample gas after reversing, lowering and raising the temperature control after the measurements of the melting point and the boiling point of the gas.

The above and other related objects and features of the invention will be apparent from a reading of the following description of the disclosure when taken together with the accompanying drawings, in which:

DESCRIPTION OF THE PREFERRED EMBODIMENTS

Figure 1:
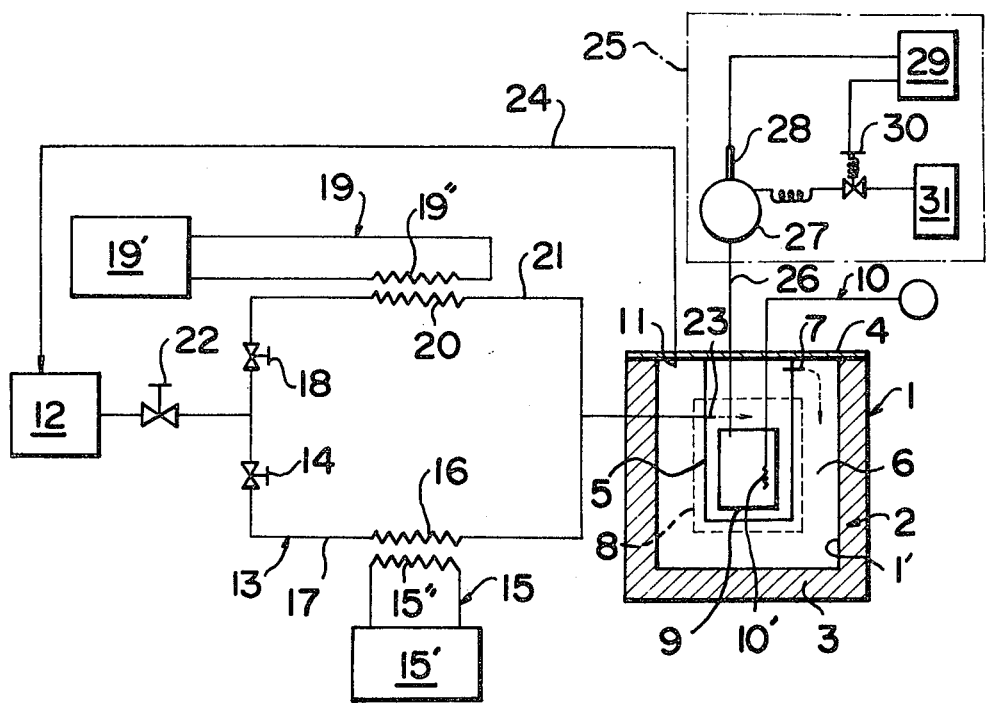
FIG. 1 is an explanatory piping diagram partly cut out of the preferred embodiment of an apparatus for measuring the melting point and the boiling point of a gas constructed according to the present invention.

Referring now to the drawings, particularly to FIG. 1, which shows a preferred embodiment of the apparatus for measuring the melting point and the boiling point of a gas constructed according to the present invention, which has a heat insulating tank 1. A heat insulating part 3 formed of a vacuum layer and a heat insulating material and so forth is formed in the body 2 of the tank 1. Tank 1 has a cover 4. An inner tank 5 is internally provided within the tank 1. A passage 6 is interposed to flow heat medium such as gas which will be hereinafter described in greater detail, between the inner tank 5 and the inner wall 1' of the tank 1. A port 7 provided at the upper part of the tank 5 communicates between the tank 5 and the passage 6, and a radiation shield 8 is provided outside the inner tank 5.

A sample cell 9 is contained within the inner tank 5 and contains a sample gas to be measured for its melting point and the boiling point, and a temperature measuring system 10 for measuring the temperature of the gas is attached to the sample cell 9 and has an external lead.

The temperature measuring system 10 may employ a reference resistance thermometer in which a reference resistor 10' is internally mounted in the sample cell 9. Passage 6 has an output 11 in the cover 4. Gas is provided from a gas source 12 in which helium or the like is filled as the heat medium and to which a piping system 13 is connected. The piping system 13 consists of a heating pipe route 17 having a heating flow rate control valve 14 manually or automatically controlled by a solenoid valve or the like and a heating heat exchanger 16 heated by a heat source 15 connected in series with the control valve 14, and a cooling pipe route 21 having a cooling flow rate control valve 18 and a cooling heat exchanger 20 cooled by a cooling source 19 connected in series with the control valve 18 as connected in parallel.

The heat source 15 may employ a heater 15" connected to a power source 15', and the cooling source 19 may employ a refrigerator 19' and a cooling zigzag tube 19" connected to the refrigerator 19'. At the inlet side of the piping system 13 is a control valve 22 such as a needle valve. The outlet 23 of the piping system 13 is inserted into the tank 1 and the inner tank 5, and thus opened above the sample cell 9. In the example shown in FIG. 1, the outlet 11 of the passage 6 is not opened externally but connected via a feedback conduit 24 to the gas source 12.

A pressure regulator 25 is connected to the sample cell 9. This regulator maintains the internal pressure of the sample cell 9 constantly or retains the internal pressure as required. In the example shown, a pressure sensor 28 is provided at a pressure regulating tank 27 which communicates through a capillary tube 26 with the sample cell 9, and a gas flow rate control valve 30 is controlled by a pressure controller 29 to which the output of the pressure sensor 28 is applied. Thus, the gas flow rate from the gas source 31 containing the pressure controlling gas to the pressure regulating tank 27 can be controlled.

The operation of the apparatus for measuring the melting point and the boiling point of the gas will now be described:

When the sample gas in the sample cell 9 is in the gaseous phase, the control valve 22 and the cooling flow rate control valve 18 are opened. The opening of the control valve 18 is manually or automatically controlled. When the heat medium from the gas source 12 is exhausted in this manner, the heat medium passing through the cooling heat exchanger 20 of the cooling pipe route 21 is cooled via the cooling source 19, and the heat medium thus cooled is discharged from the outlet 23 of the piping system 13 into the inner tank 5.

Thus, the sample cell 9 contained within the inner tank 5 is cooled by the cooling heat medium thus exhausted to cool the sample gas, and the cooling heat medium thus cooled is circulated through the port 7, passage 6, outlet 11 and feedback conduit 24 to the gas source 12 to be reused.

Figure 2:
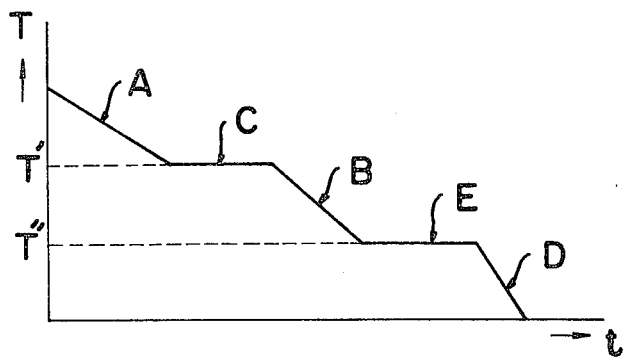
FIG. 2 is a graphical representation indicating the temperature T of a sample gas with respect to the time t in the case where the melting point and the boiling point of the gas are measured by the apparatus of this invention.

The gaseous phase sample gas is thus cooled, and the heat medium flow rate via the cooling flow rate control valve 18 can thus be controlled. When the sample gas is thus cooled as indicated in FIG. 2, even if the heat medium is cooled to low temperature in the case that the gas is transformed from the gaseous phase A to the liquid phase B, the sample gas maintains a constant temperature state C due to the latent heat. When the temperature of the sample gas of the state C is read by the temperature measuring system 10, the boiling point T' of the gas can be obtained.

When the sample gas temperature is cooled to a temperature near the boiling point T', the heat medium flow rate via the cooling flow rate control valve 18 is gradually controlled so that the temperature change of 0.1° C. per 10 to 20 minutes occurs, and the boiling point T' is thus retained constant and can be precisely obtained and confirmed.

When the sample gas in the liquid phase B is further cooled by the control, a constant temperature state E can be presented before it turns into the solid phase D, and the melting point T" can be similarly measured.

When the sample gas is in the solid phase D or the liquid phase B, the cooling flow rate control valve 18 is closed and the heating flow rate control valve 14 is opened, and the sample gas can be heated to a high temperature. Thus, the sample gas can be transformed vice versa, i.e., in reverse phase change to the previous status change, and the melting point and the boiling point of the gas can thus be measured.

It is preferred to use the same pressure controlling gas as the sample gas when the pressure regulator 25 is employed.

It should be understood from the foregoing description that since the inner tank 5 is provided via the passage 6 of the heat medium between the heat insulating tank 1 and the inner wall 1', the sample cell 9 having the temperature measuring system 10 of the sample gas charged therein is contained within the inner tank 5 and the heat medium is introduced from the outlet 23 of the piping system 13 into the inner tank 5 as was hereinbefore described, the temperature of the sample gas is not varied by the thermal effect of the external temperature, but can be precisely controlled to a predetermined temperature. It should also be appreciated that since the piping system 13 connected to the gas source 12 of the heat medium consists of parallel heating pipe route 17 and a cooling pipe route 21, the heating pipe route 17 has the heating flow rate control valve 14 and the heating heat exchanger 16 heated by the heat source 15 connected in series with the control valve 14 and the cooling pipe route 21 has a cooling flow rate control valve 18 and the cooling heat exchanger 20 cooled by a cooling source 19 connected in series with the control valve 18, the temperature of the sample gas can be raised or lowered as desired by controlling the opening of the control valves 14, 18 with the fine adjustments of the temperature change of the gas and thus a highly precise melting point and boiling point of the gas can be measured and yet the temperature of the sample gas can be raised or lowered in accordance with the phase state of the sample gas and it is possible to measure the melting point or the boiling point of the gas with rapid and simple operations. It should also be observed that since the melting point and the boiling point of the same sample gas is measured after reversing, lowering and raising temperature control after the measurements of the melting point and the boiling point of the gas, the measured results are reliable.

What is claimed is:
1. An apparatus for measuring the melting point and the boiling point of a gas, comprising in combination:
   (a) a heat insulating outer tank (1) with an inner wall (1');
   (b) an inner tank (5) within said outer tank (1), a heat medium passage (6) defined between said inner tank (5) and said inner wall (1');
   (c) a sample cell (9) for holding a gas sample, said sample cell (9) being within said inner tank (5), a gas temperature measuring instrument (10) disposed to measure the temperature of said sample gas within said sample cell;
   (d) an inert reference gas source (12), a piping system (13) connecting said inert gas source to said inner tank (5) including an inert gas outlet (23) within said inner tank (5), a heating path (17) with a first valve (14) and a cooling path (21) with a second valve (18), said paths (17, 21) extending between said inert gas source (12) and said outlet (23), heating means (15, 16) adjacent and operatively coupled to said heating path (17) to heat inert gas flowing along said heating path (17) from said inert gas source (12) and said outlet (23), and cooling means (19, 20) for cooling inert gas flowing along said cooling path (21); and,
   (e) gas pressure regulating means (25) coupled to said sample cell (9) including a pressure sensor (28), a pressure controller (29) and, a pressure regulating tank (27);
   whereby, the inert gas is flowed and regulated through both the heating and cooling paths (17, 21), and the pressure is regulated by said pressure regulating means (25), so that the melting point and the boiling point can be measured and ascertained.

* * * * *